(12) United States Patent
He et al.

(10) Patent No.: US 10,070,782 B2
(45) Date of Patent: Sep. 11, 2018

(54) ADAPTIVE OPTICAL RETINA IMAGING DEVICE AND METHOD

(71) Applicant: The Institute of Optics and Electronics, The Chinese Academy of Sciences, Chengdu, Sichuan (CN)

(72) Inventors: Yi He, Sichuan (CN); Guohua Shi, Sichuan (CN); Jinsheng Yang, Sichuan (CN); Ling Wei, Sichuan (CN); Xiqi Li, Sichuan (CN); Zhibin Wang, Sichuan (CN); Yudong Zhang, Sichuan (CN)

(73) Assignee: The Institute of Optics and Electronics, The Chinese Academy of Sciences, Chengdu, Sichuan (CN)

( * ) Notice: Subject to any disclaimer, the term of this patent is extended or adjusted under 35 U.S.C. 154(b) by 173 days.

(21) Appl. No.: 15/138,620

(22) Filed: Apr. 26, 2016

(65) Prior Publication Data

US 2016/0317030 A1    Nov. 3, 2016

(30) Foreign Application Priority Data

Apr. 29, 2015  (CN) .......................... 2015 1 0212753

(51) Int. Cl.
| | |
|---|---|
| *A61B 3/14* | (2006.01) |
| *A61B 3/10* | (2006.01) |
| *G02B 27/00* | (2006.01) |
| *A61B 3/00* | (2006.01) |
| *G02B 21/00* | (2006.01) |
| *A61B 3/12* | (2006.01) |
| *G02B 26/10* | (2006.01) |

(52) U.S. Cl.
CPC .......... *A61B 3/1015* (2013.01); *A61B 3/0091* (2013.01); *A61B 3/102* (2013.01);
(Continued)

(58) Field of Classification Search
CPC ..... A61B 3/1025; A61B 3/1015; A61B 3/102; A61B 3/0091; A61B 3/1225; A61B 3/14;
(Continued)

(56) References Cited

U.S. PATENT DOCUMENTS

| | | | |
|---|---|---|---|
| 2007/0216866 A1 | 9/2007 | Kobayashi et al. | |
| 2008/0218694 A1* | 9/2008 | Chen ................. | G02B 26/0833 351/206 |

FOREIGN PATENT DOCUMENTS

| | | |
|---|---|---|
| CN | 101869466 A | 10/2010 |
| CN | 101947158 A | 1/2011 |

(Continued)

OTHER PUBLICATIONS

Chinese Office Action for corresponding Chinese Patent Application No. 201510212753.3 dated Dec. 30, 2015, 11 pages.

*Primary Examiner* — Brandi Thomas
(74) *Attorney, Agent, or Firm* — Merchant & Gould P.C.

(57) ABSTRACT

The present disclosure provides an adaptive optical retina imaging apparatus and method. The adaptive optical retina imaging apparatus comprises an optical processing unit, an adaptive optical unit, a two-dimensional scanning unit and a primary aberration correcting unit, in which an imaging unit included in the optical processing unit is imaging based on the signal after high order aberration compensation and low order aberration compensation. By combining the adaptive optical technique, a con-focal scanning technique and the optical coherence tomography technique, two wave front sensors are utilized to detect wave front aberrations between the con-focal scanning optical path and the optical coherence tomography optical path and two wave front correctors are utilized to correct low order aberration and high order aberration of human's eyes, so as to implement low order aberration and high order aberration for the two optical paths and to implement imaging of human's eyes in a higher transverse resolution and a higher longitudinal resolution.

10 Claims, 2 Drawing Sheets

(52) U.S. Cl.
CPC .......... *A61B 3/1025* (2013.01); *A61B 3/1225* (2013.01); *G02B 21/0012* (2013.01); *G02B 27/0068* (2013.01); *G02B 26/101* (2013.01)

(58) Field of Classification Search
CPC ... A61B 3/0008; A61B 3/0033; A61B 3/0041; A61B 3/028; A61B 3/18; A61B 5/0022; A61B 5/7405; A61B 90/361; G02B 27/0068; G02B 17/0836; G02B 21/0012; G02B 21/06; G02B 21/14; G02B 26/0833; G02B 26/101; G02B 27/40; G02B 27/50
USPC ........ 351/200, 205, 203, 209–211, 221, 222, 351/243–247
See application file for complete search history.

(56) References Cited

FOREIGN PATENT DOCUMENTS

| | | |
|---|---|---|
| CN | 102038490 A | 5/2011 |
| CN | 102860816 A | 1/2013 |
| CN | 103385691 A | 11/2013 |
| EP | 2 829 220 A1 | 1/2015 |
| WO | 2007/023300 A1 | 3/2007 |
| WO | 2011/091253 A2 | 7/2011 |

\* cited by examiner

ADAPTIVE OPTICAL RETINA IMAGING DEVICE AND METHOD

This application claims benefit of Serial No. 201510212753.3, filed 29 Apr. 2015 in China and which application is incorporated herein by reference. A claim of priority is made to each of the above disclosed applications.

TECHNICAL FIELD

The present disclosure generally relates to a field of adaptive optics, and more particularly, to an adaptive optical retinal imaging device and method with a high resolution and in multiple modes.

BACKGROUND

The adaptive optics technique has a capability of measuring in real time and correcting a dynamic wave front aberration. It may correct the aberration of human's eyes which randomly varies in time and in space, so as to implement a retinal imaging for human's eyes with a high resolution approaching to a diffraction limit. At present, the technique of the adaptive optical aberration correction on the human's eyes has been used for a number of optical retina imaging techniques and becomes a necessary technical means for a retinal imaging in eye ground with a high resolution.

At present, an adaptive optical technical for correcting aberrations of human's eyes has been widely applied to various optical retina imaging technique and becomes a necessary technical means for the imaging of retinal in the eye ground with a high resolution. It forms a retinal imaging system with a high resolution such as an adaptive optical microscope for the eye ground, an adaptive optical con-focal scanning detector for eyes and an adaptive optical coherence tomography imaging system.

The retina imaging systems with a high resolution by incorporating the adaptive optical technique have independent advantages, and none of the single system may completely implement a retina imaging with high horizontal and longitudinal resolutions. At present, it is trended to incorporate various retinal imaging techniques in the adaptive optical technique to form an image in a high resolution and in multiple modes.

One patent application of WO2007/023300A1 is the first granted patent of a multifunctional retina imaging system with a high resolution based on the adaptive optical technique, which combines a con-focal scanning technique and the optical coherence tomography technique and synchronously utilizes an adaptive optical technique to correct aberrations of human's eyes, and may implement optical coherence tomography imaging and con-focal scanning imaging of the retina in a high resolution. However, such an invention only combines the adaptive optical technique and the optical coherence tomography technique, and the con-focal scanning imaging technique assists to form an image. Since its adaptive optical system can't completely correct the wave front aberration in the visual field for the con-focal scanning imaging, its horizontal resolution is insufficient.

One Chinese patent publication CN101869466A proposes to combine the adaptive optical technique, the con-focal scanning technique and the optical coherence tomography technique, which utilizes one single wave front corrector to implement a 3D imaging of the retina of human's eyes in a high resolution. However, based on statistics, the aberration of human's eyes mainly comprises a large low-order aberration and a small high-order aberration. The low-order aberration fluctuates over persons, the defocusing of which may be ±10 D, and the astigmatism may be ±5 D. The range for correcting aberration of the imaging system by only utilizing one single wave front corrector can't meet the requirements of correcting aberrations for different persons and the residual aberration greatly influence the imaging resolution, which needs to be solved.

One patent application of WO 2011/091253A2 utilizes one wave front detector to detect the wave front and controls two wave front corrects connected in series to correct the wave front aberration, so as to implement a multifunctional imaging of the optical coherence tomography technique and the con-focal scanning technique in a high resolution. However, the detection amount of the wave front for such a system can't decompose the respective wave front aberrations for the con-focal scanning light path and the optical coherence tomography imaging light path, so that its precision for correcting the aberration is low. Meanwhile, such a system has a complex configuration, a difficult controllability and a low utilization ratio of light energy, which affects efficiency of imaging in a high resolution.

One previous Chinese patent publication of CN102860816A for the same applicant of the present disclosure provides to combine the adaptive optical con-focal scanning imaging the adaptive optical coherence tomography imaging by utilizing two wave front correctors to correct the low-order and high-order aberrations of human's eyes, so that a 3D imaging of the retina of human's eyes in a high resolution can be implemented. However, such a system only utilizes one single wave front and can't implement separation of the wave front aberrations for the con-focal scanning light path and the optical coherence tomography imaging, so that the obtained low precision for correcting the aberration affects the imaging resolution. Meanwhile, the system is lack of pupil and pupil plane monitoring means so as the use of the system is inconvenient and its imaging efficiency is lower.

SUMMARY

In view of the above mentioned issues, an object of the present disclosure is to provide an adaptive optical retinal imaging device and method with a high resolution and a high precision for correcting aberration.

According to an aspect of the present disclosure, there is provided an adaptive optical retina imaging device, which comprises the following components:

a light processing unit including a plurality of light emitting units configured to emit light; a plurality of detection unit configured to detect wave front of the light; an imaging unit configured to implement a con-focal scanning imaging and an optical coherence tomography imaging;

an adaptive optical unit configured to compensate a high-order aberration of human's eyes by a wave front corrector in a primary aberration correction unit based on information about the wave front obtained during the con-focal scanning imaging and an optical coherence tomography imaging by the detection unit of the light processing unit;

a two dimensional scanning unit configured to dimensionally scan the light from the adaptive optical unit and direct the light to the primary aberration correction unit so as to irradiate a light beam for the con-focal scanning imaging and an optical coherence tomography imaging into the human's yes to illustrate the retina;

the primary aberration correction unit comprising a wave front corrector configured to compensate a low-order aberration of human's eyes based on information about the wave front obtained by the detection unit of the light processing unit;

Among others, the imaging unit implements imaging based on the detection signal after compensating the high-order aberration and the low-order aberration.

The adaptive optical retina imaging device further comprises a visual target and pupil monitoring unit including: a beacon light source configured to generate a light; and a set of focusing lens configured to convert the light generated by the beacon light source into a parallel light beam.

The visual target and pupil monitor unit further comprises a linear guide rail, along which the set of focusing lens slide to generate the visual targets with different defocuses.

The primary aberration correction unit further comprises a group of planar reflective mirrors configured to correct an aberration of defocusing.

When the detection unit in the light processing unit receives a far field point diffusion function, the low-order aberration information is obtained by calculation and is compensated by the wave front corrector contained in the primary aberration adjustment unit.

the light processing unit comprises: a first wave front sensor configured to detect wave front information containing the high-order aberration and resulting from the con-focal scanning imaging; a second wave front sensor configured to detect wave front information containing the high-order aberration and resulting from the optical coherence tomography imaging, wherein the adaptive optical unit compensates the high-order aberration for the human's eyes based on the wave front information containing the high-order aberration of the first wave front sensor and the wave front information containing the high-order aberration of the second wave front sensor.

The wave front sensor is selected from a Hartmann wave front sensor based on a micro-prism array, a Hartmann wave front sensor based on a micro-lens array, a pyramid sensor, and a curvature sensor.

The wave front corrector is selected from a deformable mirror, a liquid crystal wave front modulator, a micro machined membrane deformable mirror, micro electromechanical deformable mirror, a bimorph deformable mirror, a liquid deformable mirror.

The detection unit is one of a micro-lens wave front sensor, a micro-prism wave front sensor, a shearing interferometry wave front sensor, a curvature sensor and pyramid sensor.

According to another aspect of the present disclosure, there is provided an adaptive optical retina imaging method comprising the following steps: emitting a detection light, which is transmitted to human's eyes by an optical means; two-dimensionally scanning the light entering the human's eyes; detecting wave front of the detection light to obtain wave front information; compensating high-order aberration of human's eyes based on wave front information during a con-focal scanning imaging and an optical coherence tomography imaging; compensating low-order aberration of human's eyes based on wave front aberration information; and imaging based on a detection signal obtained after compensating the high-order and low-order aberration.

As compared with the retina imaging of the existing human's eyes, the adaptive optical retina imaging device according to the present disclosure combines the adaptive optics technique, the con-focal scanning imaging technique and the optical coherence tomography imaging technique together to completely utilize advantages of aberration correction with high prevision for the adaptive optics to implement the imaging of human's eyes with a horizontal and longitudinal high resolution. Thus, the application of the system is enhanced.

BRIEF DESCRIPTION OF THE DRAWINGS

The above and other objects, features and advantages of the present disclosure will become more apparent from the following descriptions of embodiments thereof, with reference to attached drawings, in which.

DETAILED DESCRIPTION

Hereinafter, embodiments of the present disclosure will be described with reference to the attached drawings. It is to be understood, however, that the following descriptions are provided only for illustrative purposes, instead of limiting the present disclosure. Further, in the following descriptions, configurations and techniques which are well known to those skilled in the art may be omitted to avoid unnecessarily obscuring the concept of the present disclosure.

In order to overcome the deficiency of the prior art, the present disclosure provides an adaptive optical retina imaging device with a high resolution and in multiple modes. By combining a number of modules, the present disclosure completely utilizes the advantage of correcting the high-order and low-order aberrations of human's eyes in a high precision by the adaptive optical technique. Meanwhile, the present disclosure incorporates a visual target for the same eye and a plurality of monitoring means, which greatly improves application ranges of the present invention. The present device can obtain high resolution results of the con-focal scanning imaging and the optical coherent tomography imaging, which in turn implements an imaging with high resolution in three-dimension.

Figure 1:
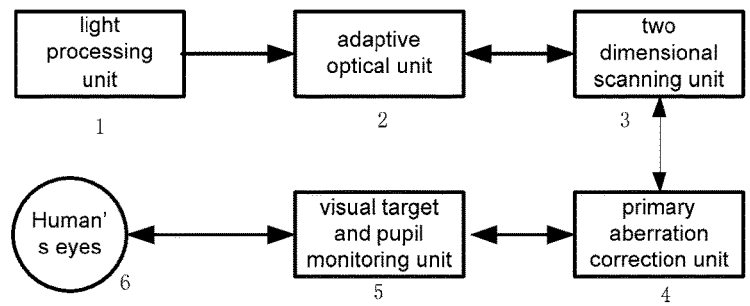
FIG. 1 is a schematic view showing a configuration of an adaptive optical retina imaging device according to an embodiment of the present disclosure.

FIG. 1 is a schematic view showing a configuration of an adaptive optical retina imaging device according to an embodiment of the present disclosure 1. The adaptive optical retina imaging device comprises a light processing unit 1, an adaptive optical unit 2, a two dimensional scanning unit 3, a primary aberration correction unit 4 and a visual target and pupil monitoring unit 5.

The light processing unit 1 includes: a plurality of light emitting units configured to emit light; a plurality of detection unit configured to detect wave front of the light including detections of high-order aberration and low-order aberration; a plurality of imaging units configured to implement imaging based on the detection signal after compensating the high-order aberration and the low-order aberration.

The adaptive optical unit 2 is configured to compensate a high-order aberration of human's eyes by a wave front corrector in a primary aberration correction unit based on information about the wave front obtained during the con-focal scanning imaging and an optical coherence tomography imaging by the detection unit of the light processing unit.

The two dimensional scanning unit 3 is configured to dimensionally scan the light from the adaptive optical unit 2 and direct the light to the primary aberration correction unit 4 so as to irradiate a light beam for the con-focal scanning imaging and an optical coherence tomography imaging into the human's yes to illustrate the retina.

The primary aberration correction unit 4 comprises a wave front corrector configured to compensate a low-order aberration of human's eyes based on information about the wave front obtained by the detection unit of the light processing unit.

The visual target and pupil monitoring unit 5 includes a beacon light source configured to generate a light; and a set of focusing lens configured to convert the light generated by the beacon light source into a parallel light beam. The visual target and pupil monitor unit 5 further comprises a linear guide rail, along which the set of focusing lens slide to generate the visual targets with different defocuses.

Figure 2:
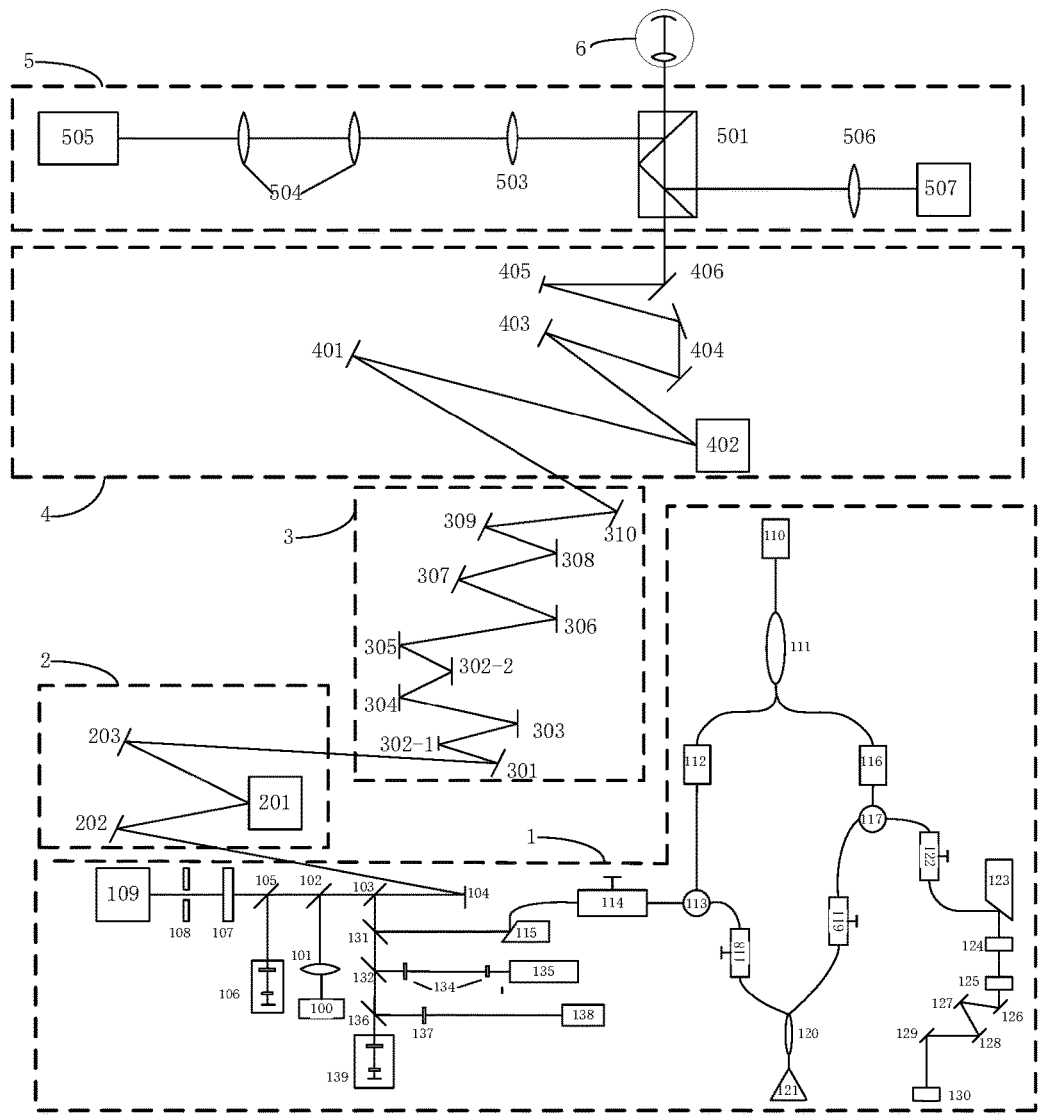
FIG. 2 is a schematic view showing a more detailed configuration of an adaptive optical retina imaging device according to an embodiment of the present disclosure.

The adaptive optical retina imaging device and method comprises the following five procedures during actual operation: a con-focal scanning imaging procedure, an optical coherence tomography imaging procedure, a lower-order aberration correcting procedure, a high-order aberration correcting procedure and a visual target and pupil monitoring procedure. The particular implementation of the present disclosure will be illustrated in detail by referring a schematic view of light path of the device as shown in FIG. 2.

Procedure of Con-Focal Scanning Imaging

A light emitted from a light source 100 with a pigtail may be deemed as a point light source, is collimated by a collimating mirror 101 into a light with a beam spot of about 6 mm, and is split by a beam splitter 102. A reflected portion of the light is transmitted through a beam splitter 103, and is matched to a wave front corrector 201 by utilizing a beam expander system constituted of a spherical reflective mirror 104 and a spherical reflective mirror 202 to expand its beam spot size, and is reflected by the wave front corrector 201. The beam is shrunk by a beam shrinking system constituted of a spherical reflective mirror 203 and a spherical reflective mirror 301 to match with a first X-direction scanning polarizer mirror 302-1 and arrives at the first X-direction scanning polarizer mirror 302-1. The incident light beam is horizontally scanned by the first X-direction scanning polarizer mirror 302-1 in a small angle, is expanded by the beam expander system constituted of a spherical reflective mirror 303 and a spherical reflective mirror 304 to match with a second X-direction scanning polarizer mirror 302-2 and arrives at the second X-direction scanning polarizer mirror 302-2. The incident light beam is horizontally scanned by the second X-direction scanning polarizer mirror 302-2 in a large angle, is expanded by the beam expander system constituted of a spherical reflective mirror 305 and a spherical reflective mirror 306 to match with a Y-direction scanning polarizer mirror 307 and arrives at the Y-direction scanning polarizer mirror 307. The incident light beam is longitudinally scanned by the Y-direction scanning polarizer mirror 307, and is reflected to a beam expander system constituted of the spherical reflective mirror 308 and the spherical reflective mirror 401. The planar mirrors 309 and 310 are inserted between the spherical reflective mirrors 308 and 401 in order to avoid blocking light. The light beam passing through the beam expanding system is continuously reflected by the wave front corrector 402 to the beam shrinking system constituted of a spherical reflective mirror 403 and the spherical reflective mirror 405 where the set of planar reflective mirrors 404 are inserted between the spherical reflective mirrors 403 and 405 so as to correct a large defocus aberration. The set of planar reflective mirrors 404 forms a badal focusing mechanism, so that a caliber of the light beam reflected by the spherical reflective 405 is matched with an entrance pupil of human's eyes and is reflected by the planar reflective mirror 406 to the dispersion prism 501 to be transmitted into the human's eyes 6, and finally focused onto one point of the retina by an optical system of the human's eyes. The eye ground of the human's eyes scatters the incident light, and the scattered light carries aberration information about the human's eyes and an intensity information at such a point on the eye ground and is returned back to the beam splitter 103 by the same way. Such a portion of the scattered light is directly reflected by the beam splitter 103 and then is split by the beam splitter 131, one part of the sample light beam is transmitted through the beam splitter 132, the beam splitter 136 and enters into the wave front controller 139; and the other part of the sample light enters into a reflective collimator 115, is coupled by an optical fiber into the polarization controller 114; and is output into the polarization controller 118 by the optical circulator 113. The polarization controller 118 controls polarization states of the sample light.

The photomultiplier 109 converts a continuous light intensity signal into an analog signal, which is input into a computer along with a synchronous voltage generated by X-direction scanning mirrors 302-1 and 302-2 and a Y-direction scanning mirror 307. Finally, information about real time intensity of some rectangular region on the retina is recovered by a computer to get an image obtained by the con-focal scanning image.

Procedure of Optical Coherence Tomography Imaging

A light emitted from a sweep frequency light source is coupled into an optical fiber coupler by optical fiber coupling and is split in a ratio of 50:50, one portion of which is propagated along the optical fiber through an acoustic-optical frequency shifter 112 into a sample arm, and the other portion of which is propagated along the optical fiber though an acoustic-optical frequency shifter 116 into a reference arm.

The reference light emergent from the acoustic-optical frequency shifter 116 is emergent through an optical circulator 117 along the optical fiber to a polarization controller 122. The polarization controller 122 controls polarization states of the light beam. The light beam emergent from the optical fiber of the polarization controller 122 and enters into a reflective collimator 123 to be collimated, and its power is controlled by a neutral density filter 124. The dispersion of the light is compensated by a water box 125 and is emergent and its light path is matched by a reference arm constituted of planar reflective mirrors 126-130. The planar reflective mirrors 126-130 in the reference arm may be added or removed according to light paths and space dimension, and the planar reflective mirror 130 is fixed to a translation stage to adjust the matching of zero light paths. The planar reflective mirror 130 reflects the reference light, the reflected reference light is returned back to the optical circulator 117 by the same way, and is emergent from the optical fiber to enter into the polarization controller 119. The polarization controller 119 adjusts the polarization states of the reference light.

The sample light emergent from the acoustic-optical frequency shifter 112 is propagated along an optical circulator 113 and is emergent to a polarization controller 114. The polarization controller 114 controls polarization states of the light beam. The light beam is emergent from the optical fiber of the polarization controller 14 and enters into a reflective collimator 115 to be collimated, and is split by a beam splitter 131. The portion of the light reflected by the beam splitter 131 is reflected by the beam splitter 103, its beam is expanded by a beam expanding system constituted of the spherical reflective mirror 104 and the spherical reflective mirror 202 to match with a deforming mirror 201, and is reflected by the deforming mirror 201. Consequently, the beam is shrunk by a beam shrinking system constituted of the spherical reflective mirror 203 and the spherical reflective mirror 301 to match with the first X-direction scanning mirror 302-1 and arrives at the first X-direction scanning mirror 302-1. The incident light beam is horizontally scanned by the first X-direction scanning polarizer mirror 302-1 in a small angle, is expanded by the beam expander system constituted of a spherical reflective mirror 303 and a spherical reflective mirror 304 to match with a second X-direction scanning polarizer mirror 302-2 and arrives at the second X-direction scanning polarizer mirror 302-2. The incident light beam is horizontally scanned by the second X-direction scanning polarizer mirror 302-2 in a large angle, is expanded by the beam expander system constituted of a spherical reflective mirror 305 and a spherical reflective mirror 306 to match with the Y-direction scanning polarizer mirror 307 and arrives at the Y-direction scanning polarizer mirror 307. The incident light beam is longitudinally scanned by the Y-direction scanning polarizer mirror 307, and is reflected to a beam expander system constituted of a spherical reflective mirror 308 and a spherical reflective mirror 401. Planar mirrors 309 and 310 are inserted between the spherical reflective mirrors 308 and 401 so as to avoid. The light beam is continuously reflected by a wave front corrector 402 to a beam shrinking system constituted of a spherical reflective mirror 403 and a spherical reflective mirror 405 where a set of planar reflective mirrors 404 are inserted between the spherical reflective mirrors 403 and 405. The set of planar reflective mirrors 404 constitute of a badal focusing mechanism. A caliber of the light beam reflected by the spherical reflective 405 is matched with an entrance pupil of human's eyes and is reflected by a planar reflective mirror 406 to a dispersion prism 501 to be transmitted into the human's eyes 6, and finally focused onto one point of the retina by an optical system of the human's eyes. The eye ground of the human's eyes scatters the incident light, and the scattered light carries aberration information about the human's eyes and an intensity information at such a point on the eye ground and is returned back to the beam splitter 103 by the same way. The beam splitter 130 splits such a portion of the scattered light as follows: the light reflected by the beam splitter 130 is transmitted through a beam splitter 131 and is continuously split by a beam splitter 132, one portion of the light split by the beam splitter 132 is focused by a lens 134 on a detector 135 to implement a detection image of the pupil plane, and another portion of the light split by the beam splitter 132 is reflected by a beam splitter 136 and is focused by a lens 137 to a detector 138 to implement a far field imaging; the light transmitted through the beam splitter 103 is transmitted through the beam splitter 120 to arrive at a beam splitter 105. The beam splitter 105 further splits this portion of scatter light, one part of which enters a wave front sensor 106, and the other of which arrives at a photomultiplier through a collective lens 107 and a pinhole 108.

The sample light beam output by the polarization controller 118 and the reference light beam output by the polarization controller 119 synchronously enter the optical fiber coupler 120 to be coupled. The light beam which is coupled by the optical fiber coupler 120 propagates through the optical fiber to a balance detector 121. The balance detector 121 extracts a coherence signal, and an image of a longitudinal cross section of the retina of human's eyes is reconstructed by the coherence signal processed by a computer in conjunction with information about scanning position, which is the optical coherence tomography imaging procedure.

Procedure of Correcting Low-Order Aberrations

The adaptive optical retina imaging device according to the present invention comprises two sets of adaptive optical system, which are configured to correct the low-order and high-order aberrations, respectively. The device for correcting the low-order aberration mainly comprises the detector 138, the badal focusing mechanism 404 and the wave front corrector 402.

When the defocusing aberration for a tester is large, a detecting precision for the wave front sensor is lower so that the aberration data is not accurate and its result can't be used to recover the wave front. The detector 138 receives a far field point spread function containing information about aberrations of human's eyes and a distance between two planar reflective mirrors of the badal focusing mechanism is adjusted so that it is observed that the point spread function received by the detector 138 is reduced, which represents that the defusing has been compensated and ensures that the state of emergent pupil will not be changed.

The far field point spread function received by the detector 138 is processed by the computer to obtain information about wave front aberrations. Furthermore, a controlling amount of wave front for correcting the wave front aberration (specially the low-order aberration containing astigmatism) is solved by the computer, is converted into a control voltage by a controlling operation and is transferred to the wave front corrector 402. The wave front corrector 402 generates opposite wave front so as to compensate the low-order aberration to implement a real time correction and compensation mainly for the low-order aberration of human's eyes.

Procedure of Correcting High-Order Aberrations

The device for implementing the procedure of correcting the high-order aberration primarily comprises the wave front sensor 106, the wave front sensor 139 and the wave front corrector 201. The wave front sensor 106 receives wave front information containing aberrations of human's eyes (especially the wave front information containing high-order aberration) in the light path for the con-focal scanning imaging, and the wave front data is transferred to the computer. The computer obtains a recovering about of the wave front by calculation, calculates the control voltage by the controlling operation and transfers the controlling voltage to the wave front corrector 201. The wave front corrector 201 generates opposite wave front so as to implement a real time correction and compensation for the aberrations of human's eyes (especially for the high-order aberration) during the procedure of the con-focal scanning imaging).

The wave front sensor 139 receives wave front information containing aberrations of human's eyes during the procedure of the optical coherence tomography imaging, especially wave front information for the high-order aberration. The wave front information for the high-order aberration is processed by the computer to obtain a controlling amount of wave front for correcting the wave front aberration, is further converted into a control voltage by a controlling operation and is transferred to the wave front corrector 201. The wave front corrector 201 generates opposite wave front so as to compensate the low-order aberration to implement a real time correction and compensation for the aberration of human's eyes during the procedure of the optical coherence tomography imaging, mainly for the high-order aberration of human's eyes.

Procedure of Visual Target and Pupil Monitoring

The device for implementing the procedure of visual target and pupil monitoring mainly comprises a visual target system, a pupil imaging system and a pupil plane imaging system. The visual target system is a visual target for the same eye and is constituted of an imaging lens 503, a set of focusing lens 504 and a LED array 505. One of the LEDs in the LED array 505 is turned on, and the light emitted from the LED passes through the set of focusing lens 504 and the imaging lens 503 to form an image at a center of macula lutea of the tester's eye. When the LEDs at different positions in the LED array are turned on, a visual axis of the tester's eye rotates along with the turned on LED, so as to observe different image regions of human's eyes and to direct rotation of human's eye to extend the function of an imaging visual field in the eye ground. The set of focusing lens 504 is configured to be slid along a linear guide rail to change a distance between two lens of the set of focusing lens 504 to generate visual targets with different defocusing amounts to implement the focusing function. A magnification ratio of imaging for the system constituted of the visual target light part and the human's eyes during focusing may be fixed if the distance between the imaging lens 503 and the set of focusing lens 504 is maintained constant during adjusting. The pupil imaging system is constituted of an imaging lens 506 and a detector 507. The light beam reflected from the pupil of human's eyes is focused to the detector 507 by the imaging lens. The detector 507 converts the optical signal into an electrical signal and outputs the electrical signal to the computer to obtain an image of pupil imaging for alignment of the imaging light beam and the pupil position of human's eyes. Meanwhile, such an alignment facilitates superposition of the pupil position of human's eyes and a position of exit pupil of the system.

The pupil plane imaging system is constituted of a set of shrinking beam lens 134 and the detector 135. In the device according to the present disclosure, the light beam reflected back from the pupil plane is reflected by the beam splitter 132, and propagates through the set of shrinking beam lens to the detector 135. The detector 135 converts optical signals into electrical signals to implement real-time monitoring and imaging for the pupil plane.

It should be noted that the present method is not limited to be implemented by the configuration as shown in FIG. 2 and may be applied for any appropriate adaptive optical retinal simulators.

Figure 3:
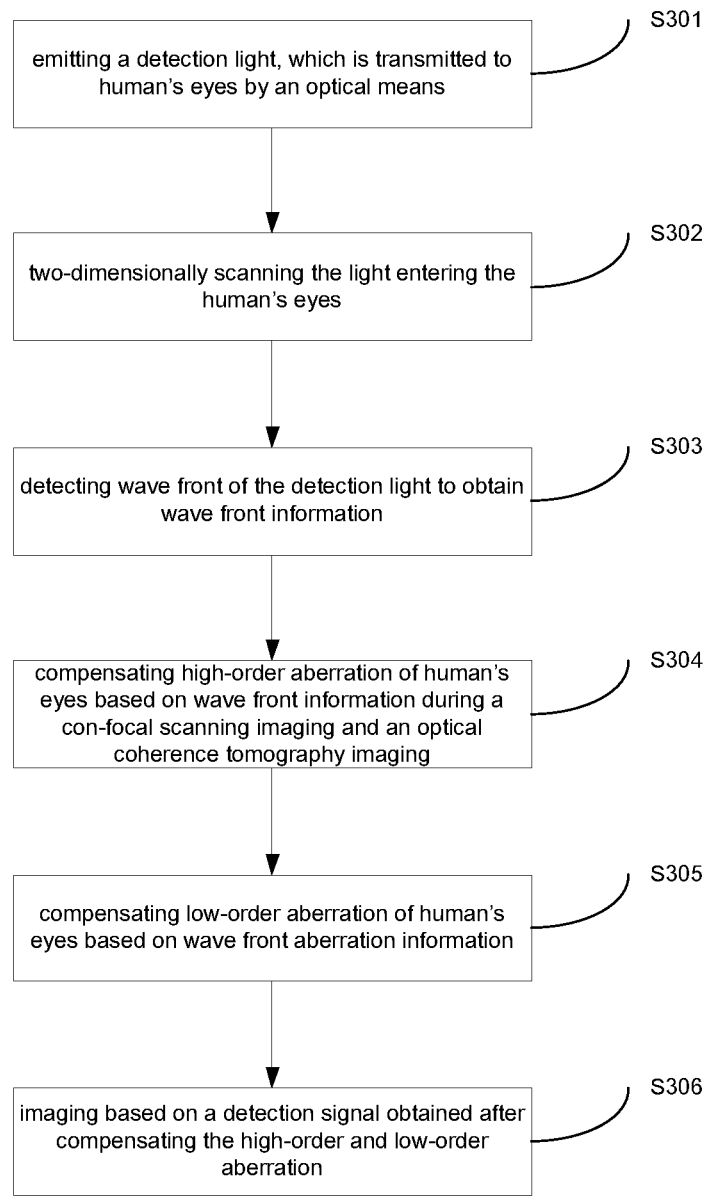
FIG. 3 is a flow chart showing an adaptive optical retina imaging method according to an embodiment of the present disclosure.

FIG. 3 shows an adaptive optical retina imaging method which comprises the following steps: emitting a detection light, which is transmitted to human's eyes by an optical means (S301); two-dimensionally scanning the light entering the human's eyes (S302); detecting wave front of the detection light to obtain wave front information (S303); compensating high-order aberration of human's eyes based on wave front information during a con-focal scanning imaging and an optical coherence tomography imaging (S304); compensating low-order aberration of human's eyes based on wave front aberration information (S305); and imaging based on a detection signal obtained after compensating the high-order and low-order aberration (S306).

As compared with the imaging technique with a high resolution for the retina of the present living human's eyes, the present disclosure has the following advantages:

The adaptive optical retina imaging device of the present disclosure in a high resolution and multiple modes combines the adaptive optical technique, a con-focal scanning technique and the optical coherence tomography technique, so as to completely utilize the advantages of the correction of aberration in high precision for the adaptive optical technique. Thus, it synchronously implements imaging of human's eyes in a high horizontal resolution and a high longitudinal resolution and enhances practicability of the system.

The adaptive optical retina imaging device of the present disclosure in a high resolution and multiple modes utilizes two wavefront sensors to correct low order aberration and high order aberration of human's eyes, which enhances ability and precision for adaptively optical correcting the wave front aberrations so as to meet the requirement of correcting aberrations for different persons.

The adaptive optical retina imaging device of the present disclosure in a high resolution and multiple modes utilizes the badal focusing mechanism constituted of two planar reflective mirrors, which may automatically compensates a defocusing amount of ±15 D.

The adaptive optical retina imaging device of the present disclosure in a high resolution and multiple modes utilizes the far field point spread function for detecting imaging to recover the wave front information, so as to use one wave front corrector to correct the low-order aberration of human's eyes and to correct the aberrations in a high precision.

The adaptive optical retina imaging device of the present disclosure in a high resolution and multiple modes utilizes two wave front sensors to detect the high-order aberrations of human's eyes during the procedures of con-focal scanning imaging and optical coherence tomography imaging, respectively, and controls the wave front corrector to correct the high-order aberrations for the two light paths, which ensures that the aberrations of the respective light paths may be corrected in a high precision.

The adaptive optical retina imaging device of the present disclosure in a high resolution and multiple modes provides a plurality of monitoring and imaging system. The visual target system may direct rotation of tester's eye to extend the function of an imaging visual field by changing of the positions of the visual target. The pupil imaging system directly forms an image for the pupil to facilitate alignment and to ensure superposition of the position of human's eyes and that of the exit pupil of the system. The pupil plane imaging system directly forms the image of the pupil to ensure a correct position of the pupil plane.

From the foregoing, it will be appreciated that specific embodiments of the disclosure have been described herein for purposes of illustration, but that various modifications, substitutions and additions may be made without deviating from the disclosure. Therefore, the technology is not limited except as by the appended claims.

We claim:

1. An adaptive optical retina imaging device, comprising:
   alight processing unit including:
   a plurality of light emitting units configured to emit light;
   a plurality of detection unit configured to detect wave front of the light;
   an imaging unit configured to implement a con-focal scanning imaging and an optical coherence tomography imaging;
   an adaptive optical unit configured to compensate a high-order aberration of human's eyes by a wave front corrector in a primary aberration correction unit based on information about the wave front obtained during the con-focal scanning imaging and an optical coherence tomography imaging by the detection unit of the light processing unit;

a two dimensional scanning unit configured to dimensionally scan the light from the adaptive optical unit and direct the light to the primary aberration correction unit so as to irradiate a light beam for the con-focal scanning imaging and an optical coherence tomography imaging into the human's yes to illustrate the retina;

the primary aberration correction unit comprising a wave front corrector configured to compensate a low-order aberration of human's eyes based on information about the wave front obtained by the detection unit of the light processing unit;

wherein the imaging unit implement imaging based on the detection signal after compensating the high-order aberration and the low-order aberration.

2. The adaptive optical retina imaging device according to claim 1, further comprising a visual target and pupil monitoring unit including:

a beacon light source configured to generate a light;

a set of focusing lens configured to convert the light generated by the beacon light source into a parallel light beam.

3. The adaptive optical retina imaging device according to claim 1, wherein the visual target and pupil monitor unit further comprises a linear guide rail, along which the set of focusing lens slide to generate the visual targets with different defocuses.

4. The adaptive optical retina imaging device according to claim 1, wherein the primary aberration correction unit further comprises a group of planar reflective mirrors configured to correct an aberration of defocusing.

5. The adaptive optical retina imaging device according to claim 1, wherein when the detection unit in the light processing unit receives a far field point diffusion function, the low-order aberration information is obtained by calculation and is compensated by the wave front corrector contained in the primary aberration adjustment unit.

6. The adaptive optical retina imaging device according to claim 1, wherein the light processing unit comprises:

a first wave front sensor configured to detect wave front information containing the high-order aberration and resulting from the con-focal scanning imaging;

a second wave front sensor configured to detect wave front information containing the high-order aberration and resulting from the optical coherence tomography imaging, wherein the adaptive optical unit compensates the high-order aberration for the human's eyes based on the wave front information containing the high-order aberration of the first wave front sensor and the wave front information containing the high-order aberration of the second wave front sensor.

7. The adaptive optical retina imaging device according to claim 1, wherein the wave front sensor is selected from a Hartmann wavefront sensor based on a micro-prism array, a Hartmann wavefront sensor based on a micro-lens array, a pyramid sensor, and a curvature sensor.

8. The adaptive optical retina imaging device according to claim 1, wherein the wavefront corrector is selected from a deformable mirror, a liquid crystal wavefront modulator, a micro machined membrane deformable mirror, micro electromechanical deformable mirror, a bimorph deformable mirror, a liquid deformable mirror.

9. The adaptive optical retina imaging device according to claim 1, wherein the detection unit is one of a micro-lens wave front sensor, a micro-prism wave front sensor, a shearing interferometry wave front sensor, a curvature sensor and pyramid sensor.

10. An adaptive optical retina imaging method, comprising:

emitting a detection light, which is transmitted to human's eyes by an optical means;

two-dimensionally scanning the light entering the human's eyes;

detecting wave front of the detection light to obtain wave front information;

compensating high-order aberration of human's eyes based on wave front information during a con-focal scanning imaging and an optical coherence tomography imaging;

compensating low-order aberration of human's eyes based on wave front aberration information; and imaging based on a detection signal obtained after compensating the high-order and low-order aberration.

* * * * *